(12) United States Patent
Pal et al.

(10) Patent No.: US 8,221,446 B2
(45) Date of Patent: Jul. 17, 2012

(54) EMBOLIC PROTECTION DEVICE

(75) Inventors: Dharmendra Pal, Wilmington, MA (US); Shyam Kuppurathanam, Indianapolis, IN (US)

(73) Assignee: Cook Medical Technologies, Bloomington, IN (US)

( * ) Notice: Subject to any disclaimer, the term of this patent is extended or adjusted under 35 U.S.C. 154(b) by 273 days.

(21) Appl. No.: 11/375,434

(22) Filed: Mar. 14, 2006

(65) Prior Publication Data

US 2006/0229660 A1    Oct. 12, 2006

Related U.S. Application Data

(60) Provisional application No. 60/661,732, filed on Mar. 15, 2005.

(51) Int. Cl.
*A61M 29/00* (2006.01)
(52) U.S. Cl. .................... 606/200; 606/191; 606/194
(58) Field of Classification Search .................. 606/198, 606/200, 191–192, 194–195; 623/23.72, 623/23.76, 1.13, 1.36
See application file for complete search history.

(56) References Cited

U.S. PATENT DOCUMENTS

| | | |
|---|---|---|
| 3,108,593 A | 10/1963 | Glassman |
| 3,334,629 A | 8/1967 | Cohn |
| 3,472,230 A | 10/1969 | Fogarty |
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |

(Continued)

FOREIGN PATENT DOCUMENTS

DE    3429850 A1    2/1986

(Continued)

OTHER PUBLICATIONS

Heeschen et al., Nature Medicine 7 (2001), No. 7, 833-839.

(Continued)

*Primary Examiner* — Corrine M McDermott
*Assistant Examiner* — Mark Mashack
(74) *Attorney, Agent, or Firm* — Brinks Hofer Gilson & Lione

(57) ABSTRACT

An embolic protection device for deployment in a body vessel is provided, including a filtering body having a lip and extending therefrom to a tail and a frame connected to the lip for supporting the filtering body. The filtering body includes first and second openings formed therethrough, the first opening having a first area for maintaining fluid flowpaths through the device, the second opening having a second area for filtering emboli in the body vessel. The first area is greater than the second area.

15 Claims, 6 Drawing Sheets

U.S. PATENT DOCUMENTS

| | | |
|---|---|---|
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A * | 9/1998 | Bachinski et al. ............. 623/1.1 |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A * | 8/1999 | Kerr ............................. 606/200 |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A * | 11/1999 | Smith .......................... 606/200 |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |

| | | | | | | |
|---|---|---|---|---|---|---|
| 6,093,199 | A | 7/2000 | Brown et al. | 6,334,864 B1 | 1/2002 | Amplatz et al. |
| 6,096,053 | A | 8/2000 | Bates | 6,336,934 B1 | 1/2002 | Gilson et al. |
| 6,096,070 | A | 8/2000 | Ragheb et al. | 6,338,739 B1 | 1/2002 | Datta et al. |
| 6,099,549 | A | 8/2000 | Bosma et al. | 6,340,364 B2 | 1/2002 | Kanesaka |
| 6,106,497 | A | 8/2000 | Wang | 6,342,062 B1 | 1/2002 | Suon et al. |
| 6,126,672 | A | 10/2000 | Berryman et al. | 6,342,063 B1 | 1/2002 | DeVries et al. |
| 6,126,673 | A | 10/2000 | Kim et al. | 6,344,048 B1 | 2/2002 | Chin et al. |
| 6,129,739 | A | 10/2000 | Khosravi | 6,344,049 B1 | 2/2002 | Levinson et al. |
| 6,136,016 | A | 10/2000 | Barbut et al. | 6,346,116 B1 | 2/2002 | Brooks et al. |
| 6,146,396 | A | 11/2000 | Konya et al. | 6,348,041 B1 | 2/2002 | Klint |
| 6,146,404 | A | 11/2000 | Kim et al. | 6,348,063 B1 | 2/2002 | Yassour et al. |
| 6,152,931 | A | 11/2000 | Nadal et al. | 6,355,051 B1 | 3/2002 | Sisskind et al. |
| 6,152,946 | A | 11/2000 | Broome et al. | 6,358,228 B1 | 3/2002 | Tubman et al. |
| 6,152,947 | A | 11/2000 | Ambrisco et al. | 6,361,545 B1 | 3/2002 | Macoviak et al. |
| 6,156,061 | A | 12/2000 | Wallace et al. | 6,361,546 B1 | 3/2002 | Khosravi |
| 6,156,062 | A | 12/2000 | McGuinness | 6,361,547 B1 | 3/2002 | Hieshima |
| 6,159,230 | A | 12/2000 | Samuels | 6,364,895 B1 | 4/2002 | Greenhalgh |
| 6,165,179 | A | 12/2000 | Cathcart et al. | 6,364,896 B1 | 4/2002 | Addis |
| 6,165,198 | A | 12/2000 | McGurk et al. | 6,368,338 B1 | 4/2002 | Konya et al. |
| 6,165,199 | A | 12/2000 | Barbut | 6,371,961 B1 | 4/2002 | Osborne et al. |
| 6,165,200 | A | 12/2000 | Tsugita et al. | 6,371,969 B1 | 4/2002 | Tsugita et al. |
| 6,168,579 | B1 | 1/2001 | Tsugita et al. | 6,371,970 B1 | 4/2002 | Khosravi et al. |
| 6,168,603 | B1 | 1/2001 | Leslie et al. | 6,371,971 B1 | 4/2002 | Tsugita et al. |
| 6,168,610 | B1 | 1/2001 | Marin et al. | 6,375,670 B1 | 4/2002 | Greenhalgh |
| 6,168,622 | B1 | 1/2001 | Mazzocchi | 6,379,374 B1 | 4/2002 | Hieshima et al. |
| 6,171,327 | B1 | 1/2001 | Daniel et al. | 6,380,457 B1 | 4/2002 | Yurek et al. |
| 6,171,328 | B1 | 1/2001 | Addis | 6,383,146 B1 | 5/2002 | Klint |
| 6,174,318 | B1 | 1/2001 | Bates et al. | 6,383,171 B1 | 5/2002 | Gifford et al. |
| 6,179,851 | B1 | 1/2001 | Barbut et al. | 6,383,174 B1 | 5/2002 | Eder |
| 6,179,859 | B1 | 1/2001 | Bates et al. | 6,383,193 B1 | 5/2002 | Cathcart et al. |
| 6,179,860 | B1 | 1/2001 | Fulton, III et al. | 6,383,196 B1 | 5/2002 | Leslie et al. |
| 6,179,861 | B1 | 1/2001 | Khosravi et al. | 6,383,205 B1 | 5/2002 | Samson et al. |
| 6,187,025 | B1 | 2/2001 | Machek | 6,383,206 B1 | 5/2002 | Gillick et al. |
| 6,193,739 | B1 | 2/2001 | Chevillon et al. | 6,391,044 B1 | 5/2002 | Yadav et al. |
| 6,203,561 | B1 | 3/2001 | Ramee et al. | 6,391,045 B1 | 5/2002 | Kim et al. |
| 6,206,931 | B1 | 3/2001 | Cook et al. | 6,391,052 B2 | 5/2002 | Buirge et al. |
| 6,214,025 | B1 | 4/2001 | Thistle et al. | 6,395,014 B1 | 5/2002 | Macoviak et al. |
| 6,214,026 | B1 | 4/2001 | Lepak et al. | 6,402,771 B1 | 6/2002 | Palmer et al. |
| 6,221,091 | B1 | 4/2001 | Khosravi | 6,402,772 B1 | 6/2002 | Amplatz et al. |
| 6,224,620 | B1 | 5/2001 | Maahs | 6,409,742 B1 | 6/2002 | Fulton, III et al. |
| 6,231,588 | B1 | 5/2001 | Zadno-Azizi | 6,413,235 B1 | 7/2002 | Parodi |
| 6,231,589 | B1 | 5/2001 | Wessman et al. | 6,416,530 B2 | 7/2002 | DeVries et al. |
| 6,235,044 | B1 | 5/2001 | Root et al. | 6,419,686 B1 | 7/2002 | McLeod et al. |
| 6,235,045 | B1 | 5/2001 | Barbut et al. | 6,423,052 B1 | 7/2002 | Escano |
| 6,238,412 | B1 | 5/2001 | Dubrul et al. | 6,423,086 B1 | 7/2002 | Barbut et al. |
| 6,241,746 | B1 | 6/2001 | Bosma et al. | 6,425,909 B1 | 7/2002 | Dieck et al. |
| 6,245,087 | B1 | 6/2001 | Addis | 6,428,557 B1 | 8/2002 | Hilaire |
| 6,245,088 | B1 | 6/2001 | Lowery | 6,428,558 B1 | 8/2002 | Jones et al. |
| 6,245,089 | B1 | 6/2001 | Daniel et al. | 6,428,559 B1 | 8/2002 | Johnson |
| 6,251,092 | B1 | 6/2001 | Qin et al. | 6,432,122 B1 | 8/2002 | Gilson et al. |
| 6,251,122 | B1 | 6/2001 | Tsukernik | 6,436,112 B2 | 8/2002 | Wensel et al. |
| 6,254,550 | B1 | 7/2001 | McNamara et al. | 6,436,120 B1 | 8/2002 | Meglin |
| 6,254,633 | B1 | 7/2001 | Pinchuk et al. | 6,436,121 B1 | 8/2002 | Blom |
| 6,258,026 | B1 | 7/2001 | Ravenscroft et al. | 6,443,926 B1 | 9/2002 | Kletschka |
| 6,258,115 | B1 | 7/2001 | Dubrul | 6,443,971 B1 | 9/2002 | Boylan et al. |
| 6,258,120 | B1 | 7/2001 | McKenzie et al. | 6,443,972 B1 | 9/2002 | Bosma et al. |
| 6,261,305 | B1 | 7/2001 | Marotta et al. | 6,447,530 B1 | 9/2002 | Ostrovsky et al. |
| 6,264,672 | B1 | 7/2001 | Fisher | 6,447,531 B1 | 9/2002 | Amplatz |
| 6,267,776 | B1 | 7/2001 | O'Connell | 6,454,775 B1 | 9/2002 | Demarais et al. |
| 6,267,777 | B1 | 7/2001 | Bosma et al. | 6,458,139 B1 | 10/2002 | Palmer et al. |
| 6,273,900 | B1 | 8/2001 | Nott et al. | 6,458,145 B1 | 10/2002 | Ravenscroft et al. |
| 6,273,901 | B1 | 8/2001 | Whitcher et al. | 6,461,370 B1 | 10/2002 | Gray et al. |
| 6,277,125 | B1 | 8/2001 | Barry et al. | 6,468,290 B1 | 10/2002 | Weldon et al. |
| 6,277,126 | B1 | 8/2001 | Barry et al. | 6,468,291 B2 * | 10/2002 | Bates et al. ................ 606/200 |
| 6,277,138 | B1 | 8/2001 | Levinson et al. | 6,482,222 B1 | 11/2002 | Bruckheimer et al. |
| 6,277,139 | B1 | 8/2001 | Levinson et al. | 6,485,456 B1 | 11/2002 | Kletschka |
| 6,280,451 | B1 | 8/2001 | Bates et al. | 6,485,500 B1 | 11/2002 | Kokish et al. |
| 6,287,321 | B1 | 9/2001 | Jang | 6,485,501 B1 | 11/2002 | Green |
| 6,290,710 | B1 | 9/2001 | Cryer et al. | 6,485,502 B2 | 11/2002 | Don Michael et al. |
| 6,299,604 | B1 | 10/2001 | Ragheb et al. | 6,491,712 B1 | 12/2002 | O'Connor |
| 6,306,163 | B1 | 10/2001 | Fitz | 6,494,895 B2 | 12/2002 | Addis |
| 6,309,399 | B1 | 10/2001 | Barbut et al. | 6,497,709 B1 | 12/2002 | Heath |
| 6,312,444 | B1 | 11/2001 | Barbut | 6,499,487 B1 | 12/2002 | McKenzie et al. |
| 6,319,268 | B1 | 11/2001 | Ambrisco et al. | 6,500,166 B1 | 12/2002 | Zadno Azizi et al. |
| 6,325,815 | B1 | 12/2001 | Kusleika et al. | 6,500,191 B2 | 12/2002 | Addis |
| 6,325,816 | B1 | 12/2001 | Fulton, III et al. | 6,502,606 B2 | 1/2003 | Klint |
| 6,328,755 | B1 | 12/2001 | Marshall | 6,506,203 B1 | 1/2003 | Boyle et al. |
| 6,331,183 | B1 | 12/2001 | Suon | 6,506,205 B2 | 1/2003 | Goldberg et al. |
| 6,331,184 | B1 | 12/2001 | Abrams | 6,508,826 B2 | 1/2003 | Murphy et al. |

| | | |
|---|---|---|
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 * | 7/2003 | Barbut et al. .................. 606/200 |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Theilen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 * | 10/2003 | Leeflang et al. .............. 606/200 |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 * | 2/2004 | Boyle et al. .................... 604/106 |
| 6,695,865 B2 * | 2/2004 | Boyle et al. .................. 606/200 |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,866,677 B2 | 3/2005 | Douk et al. |
| 6,866,680 B2 | 3/2005 | Yassour et al. |
| 6,896,691 B2 | 5/2005 | Boylan et al. |
| 6,929,709 B2 | 8/2005 | Smith |
| 6,932,831 B2 | 8/2005 | Forber |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van Der Burg et al. |
| 7,189,249 B2 | 3/2007 | Hart et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,766,934 B2 | 8/2010 | Pal et al. |
| 7,918,882 B2 * | 4/2011 | Pavcnik et al. ............... 623/1.13 |
| 8,133,253 B2 * | 3/2012 | Bosma et al. .................. 606/200 |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |

| | | | | | |
|---|---|---|---|---|---|
| 2001/0016755 A1 | 8/2001 | Addis | 2002/0133191 A1 | 9/2002 | Khosravi et al. |
| 2001/0020175 A1 | 9/2001 | Yassour et al. | 2002/0133192 A1 | 9/2002 | Kusleika et al. |
| 2001/0023358 A1 | 9/2001 | Tsukernik | 2002/0138094 A1 | 9/2002 | Borillo et al. |
| 2001/0025187 A1 | 9/2001 | Okada | 2002/0138095 A1 | 9/2002 | Mazzocchi et al. |
| 2001/0031980 A1 | 10/2001 | Wensel et al. | 2002/0138096 A1 | 9/2002 | Hieshima |
| 2001/0031981 A1 | 10/2001 | Evans et al. | 2002/0138097 A1 | 9/2002 | Ostrovsky et al. |
| 2001/0031982 A1 | 10/2001 | Peterson et al. | 2002/0143360 A1 | 10/2002 | Douk et al. |
| 2001/0039431 A1 | 11/2001 | DeVries et al. | 2002/0143361 A1 | 10/2002 | Douk et al. |
| 2001/0039432 A1 | 11/2001 | Whitcher et al. | 2002/0143362 A1 | 10/2002 | Macoviak et al. |
| 2001/0041908 A1 | 11/2001 | Levinson et al. | 2002/0151927 A1 | 10/2002 | Douk et al. |
| 2001/0041909 A1* | 11/2001 | Tsugita et al. ............... 606/200 | 2002/0151928 A1 | 10/2002 | Leslie et al. |
| 2001/0041928 A1 | 11/2001 | Pavcnik et al. | 2002/0156520 A1 | 10/2002 | Boylan et al. |
| 2001/0044632 A1 | 11/2001 | Daniel et al. | 2002/0161389 A1 | 10/2002 | Boyle et al. |
| 2001/0044634 A1 | 11/2001 | Don Michael et al. | 2002/0161390 A1 | 10/2002 | Mouw |
| 2001/0053921 A1 | 12/2001 | Jang | 2002/0161391 A1 | 10/2002 | Murphy et al. |
| 2002/0002383 A1 | 1/2002 | Sepetka et al. | 2002/0161392 A1 | 10/2002 | Dubrul |
| 2002/0002384 A1 | 1/2002 | Gilson et al. | 2002/0161393 A1 | 10/2002 | Demond et al. |
| 2002/0004667 A1 | 1/2002 | Adams et al. | 2002/0161394 A1 | 10/2002 | Macoviak et al. |
| 2002/0016564 A1 | 2/2002 | Courtney et al. | 2002/0161395 A1 | 10/2002 | Douk et al. |
| 2002/0016609 A1 | 2/2002 | Wensel et al. | 2002/0161396 A1 | 10/2002 | Jang et al. |
| 2002/0022858 A1 | 2/2002 | Demond et al. | 2002/0165557 A1 | 11/2002 | McAlister |
| 2002/0022859 A1 | 2/2002 | Hogendijk | 2002/0165573 A1 | 11/2002 | Barbut |
| 2002/0026211 A1 | 2/2002 | Khosravi et al. | 2002/0165576 A1* | 11/2002 | Boyle et al. .................. 606/200 |
| 2002/0026212 A1 | 2/2002 | Wholey et al. | 2002/0165598 A1 | 11/2002 | Wahr et al. |
| 2002/0026213 A1 | 2/2002 | Gilson et al. | 2002/0169472 A1 | 11/2002 | Douk et al. |
| 2002/0032460 A1 | 3/2002 | Kusleika et al. | 2002/0169474 A1 | 11/2002 | Kusleika et al. |
| 2002/0032461 A1 | 3/2002 | Marshall | 2002/0173815 A1 | 11/2002 | Hogendijk et al. |
| 2002/0042626 A1 | 4/2002 | Hanson et al. | 2002/0173819 A1 | 11/2002 | Leeflang et al. |
| 2002/0042627 A1 | 4/2002 | Brady et al. | 2002/0177872 A1 | 11/2002 | Papp et al. |
| 2002/0045915 A1 | 4/2002 | Balceta et al. | 2002/0177899 A1 | 11/2002 | Eum et al. |
| 2002/0045916 A1 | 4/2002 | Gray et al. | 2002/0183781 A1 | 12/2002 | Casey et al. |
| 2002/0045918 A1 | 4/2002 | Suon et al. | 2002/0183782 A1* | 12/2002 | Tsugita et al. ............... 606/200 |
| 2002/0049452 A1 | 4/2002 | Kurz et al. | 2002/0183783 A1 | 12/2002 | Shadduck |
| 2002/0049468 A1 | 4/2002 | Streeter et al. | 2002/0188313 A1 | 12/2002 | Johnson et al. |
| 2002/0052627 A1 | 5/2002 | Boylan et al. | 2002/0188314 A1 | 12/2002 | Anderson et al. |
| 2002/0058904 A1 | 5/2002 | Boock et al. | 2002/0193824 A1 | 12/2002 | Boylan et al. |
| 2002/0058911 A1 | 5/2002 | Gilson et al. | 2002/0193825 A1 | 12/2002 | McGuckin et al. |
| 2002/0058963 A1 | 5/2002 | Vale et al. | 2002/0193826 A1 | 12/2002 | McGuckin et al. |
| 2002/0058964 A1 | 5/2002 | Addis | 2002/0193827 A1 | 12/2002 | McGuckin et al. |
| 2002/0062133 A1 | 5/2002 | Gilson et al. | 2002/0193828 A1* | 12/2002 | Griffin et al. ................. 606/200 |
| 2002/0062134 A1 | 5/2002 | Barbut et al. | 2002/0198561 A1 | 12/2002 | Amplatz |
| 2002/0062135 A1 | 5/2002 | Mazzocchi et al. | 2003/0004536 A1 | 1/2003 | Boylan et al. |
| 2002/0065507 A1 | 5/2002 | Zadno-Azizi | 2003/0004537 A1 | 1/2003 | Boyle et al. |
| 2002/0068954 A1 | 6/2002 | Foster | 2003/0004538 A1 | 1/2003 | Secrest et al. |
| 2002/0068955 A1 | 6/2002 | Khosravi | 2003/0004539 A1 | 1/2003 | Linder et al. |
| 2002/0072764 A1 | 6/2002 | Sepetka et al. | 2003/0004540 A1 | 1/2003 | Linder et al. |
| 2002/0072765 A1 | 6/2002 | Mazzocchi et al. | 2003/0004541 A1 | 1/2003 | Linder et al. |
| 2002/0077596 A1 | 6/2002 | McKenzie et al. | 2003/0004542 A1 | 1/2003 | Wensel et al. |
| 2002/0082558 A1 | 6/2002 | Samson et al. | 2003/0009146 A1 | 1/2003 | Muni et al. |
| 2002/0082639 A1 | 6/2002 | Broome et al. | 2003/0009189 A1 | 1/2003 | Gilson et al. |
| 2002/0087187 A1 | 7/2002 | Mazzocchi et al. | 2003/0009190 A1 | 1/2003 | Kletschka et al. |
| 2002/0090389 A1 | 7/2002 | Humes et al. | 2003/0009191 A1 | 1/2003 | Wensel et al. |
| 2002/0091407 A1 | 7/2002 | Zadno-Azizi et al. | 2003/0014072 A1 | 1/2003 | Wensel et al. |
| 2002/0091408 A1 | 7/2002 | Sutton et al. | 2003/0018354 A1 | 1/2003 | Roth et al. |
| 2002/0091409 A1 | 7/2002 | Sutton et al. | 2003/0018355 A1 | 1/2003 | Goto et al. |
| 2002/0095170 A1 | 7/2002 | Krolik et al. | 2003/0023263 A1 | 1/2003 | Krolik et al. |
| 2002/0095171 A1* | 7/2002 | Belef ......................... 606/200 | 2003/0023264 A1 | 1/2003 | Dieck et al. |
| 2002/0095172 A1 | 7/2002 | Mazzocchi et al. | 2003/0023265 A1* | 1/2003 | Forber ........................ 606/200 |
| 2002/0095173 A1 | 7/2002 | Mazzocchi et al. | 2003/0032976 A1 | 2/2003 | Boucek |
| 2002/0095174 A1 | 7/2002 | Tsugita et al. | 2003/0032977 A1 | 2/2003 | Brady |
| 2002/0099405 A1 | 7/2002 | Yurek et al. | 2003/0040772 A1 | 2/2003 | Hyodoh et al. |
| 2002/0099407 A1 | 7/2002 | Becker et al. | 2003/0045897 A1 | 3/2003 | Huter et al. |
| 2002/0099435 A1 | 7/2002 | Stinson | 2003/0045898 A1 | 3/2003 | Harrison et al. |
| 2002/0103501 A1 | 8/2002 | Diaz et al. | 2003/0050662 A1 | 3/2003 | Don Michael |
| 2002/0107541 A1 | 8/2002 | Vale et al. | 2003/0055452 A1 | 3/2003 | Joergensen et al. |
| 2002/0111647 A1 | 8/2002 | Khairkhahan et al. | 2003/0055480 A1 | 3/2003 | Fischell et al. |
| 2002/0111648 A1 | 8/2002 | Kusleika et al. | 2003/0060843 A1 | 3/2003 | Boucher |
| 2002/0111649 A1 | 8/2002 | Russo et al. | 2003/0060844 A1 | 3/2003 | Borillo et al. |
| 2002/0116024 A1 | 8/2002 | Goldberg et al. | 2003/0065354 A1 | 4/2003 | Boyle et al. |
| 2002/0120226 A1 | 8/2002 | Beck | 2003/0065355 A1 | 4/2003 | Weber |
| 2002/0120286 A1 | 8/2002 | DoBrava et al. | 2003/0065356 A1 | 4/2003 | Tsugita et al. |
| 2002/0120287 A1 | 8/2002 | Huter | 2003/0069596 A1 | 4/2003 | Eskuri |
| 2002/0123720 A1 | 9/2002 | Kusleika et al. | 2003/0073979 A1 | 4/2003 | Naimark et al. |
| 2002/0123755 A1 | 9/2002 | Lowe et al. | 2003/0074019 A1 | 4/2003 | Gray et al. |
| 2002/0123759 A1 | 9/2002 | Amplatz | 2003/0078614 A1 | 4/2003 | Salahieh et al. |
| 2002/0123766 A1 | 9/2002 | Seguin et al. | 2003/0083608 A1 | 5/2003 | Evans et al. |
| 2002/0128679 A1 | 9/2002 | Turovskiy et al. | 2003/0083692 A1 | 5/2003 | Vrba et al. |
| 2002/0128680 A1 | 9/2002 | Pavlovic | 2003/0083693 A1 | 5/2003 | Daniel et al. |
| 2002/0128681 A1 | 9/2002 | Broome et al. | 2003/0088211 A1 | 5/2003 | Anderson et al. |

| | | |
|---|---|---|
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 * | 7/2003 | Levinson et al. ............ 606/200 |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Hunter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 * | 5/2004 | Leeflang et al. ............ 606/200 |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 * | 11/2004 | Krolik et al. ................. 606/200 |
| 2004/0236369 A1 | 11/2004 | Dubrul |
| 2005/0004663 A1 | 1/2005 | Llanos et al. |
| 2005/0027345 A1 | 2/2005 | Horan et al. |
| 2005/0038468 A1 | 2/2005 | Panetta et al. |
| 2005/0038503 A1 | 2/2005 | Greenhalgh |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |

| | | | |
|---|---|---|---|
| 2006/0009799 A1* | 1/2006 | Kleshinski et al. ........... 606/200 | |
| 2006/0020334 A1 | 1/2006 | Lashinski et al. | |
| 2006/0030923 A1 | 2/2006 | Gunderson | |
| 2006/0074474 A1 | 4/2006 | Theron | |
| 2006/0100544 A1 | 5/2006 | Ayala et al. | |
| 2006/0100545 A1 | 5/2006 | Ayala et al. | |
| 2006/0184194 A1 | 8/2006 | Pal et al. | |
| 2006/0200221 A1 | 9/2006 | Malewicz | |
| 2006/0229660 A1 | 10/2006 | Pal et al. | |
| 2006/0264707 A1 | 11/2006 | Kinney | |
| 2006/0287668 A1 | 12/2006 | Fawzi et al. | |
| 2007/0038241 A1 | 2/2007 | Pal | |
| 2007/0100372 A1 | 5/2007 | Schaeffer | |
| 2007/0112374 A1 | 5/2007 | Paul, Jr. et al. | |
| 2007/0129752 A1 | 6/2007 | Webler et al. | |
| 2007/0167974 A1 | 7/2007 | Cully et al. | |
| 2007/0185521 A1 | 8/2007 | Bui et al. | |
| 2007/0288054 A1 | 12/2007 | Tanaka et al. | |
| 2008/0015518 A1 | 1/2008 | Huang et al. | |
| 2008/0027481 A1 | 1/2008 | Gilson et al. | |
| 2008/0154236 A1 | 6/2008 | Elkins et al. | |
| 2008/0167629 A1 | 7/2008 | Dann et al. | |
| 2008/0167677 A1* | 7/2008 | Vale et al. ................. 606/200 | |
| 2008/0255587 A1 | 10/2008 | Cully et al. | |
| 2008/0255606 A1 | 10/2008 | Mitra et al. | |
| 2008/0262337 A1 | 10/2008 | Falwell et al. | |
| 2008/0275569 A1 | 11/2008 | Lesh | |
| 2010/0222805 A1* | 9/2010 | Pal et al. .................. 606/200 | |
| 2011/0098738 A1* | 4/2011 | Hunt ........................ 606/200 | |

FOREIGN PATENT DOCUMENTS

| | | |
|---|---|---|
| EP | 1127556 A2 | 8/2001 |
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |

OTHER PUBLICATIONS

Johnson et al., Circulation Research 94 (2004), No. 2, 262-268.
Rubicon Embolic Filter, The Next Generation of EM, Rubicon Medical, www.rubiconmed.com.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.

* cited by examiner

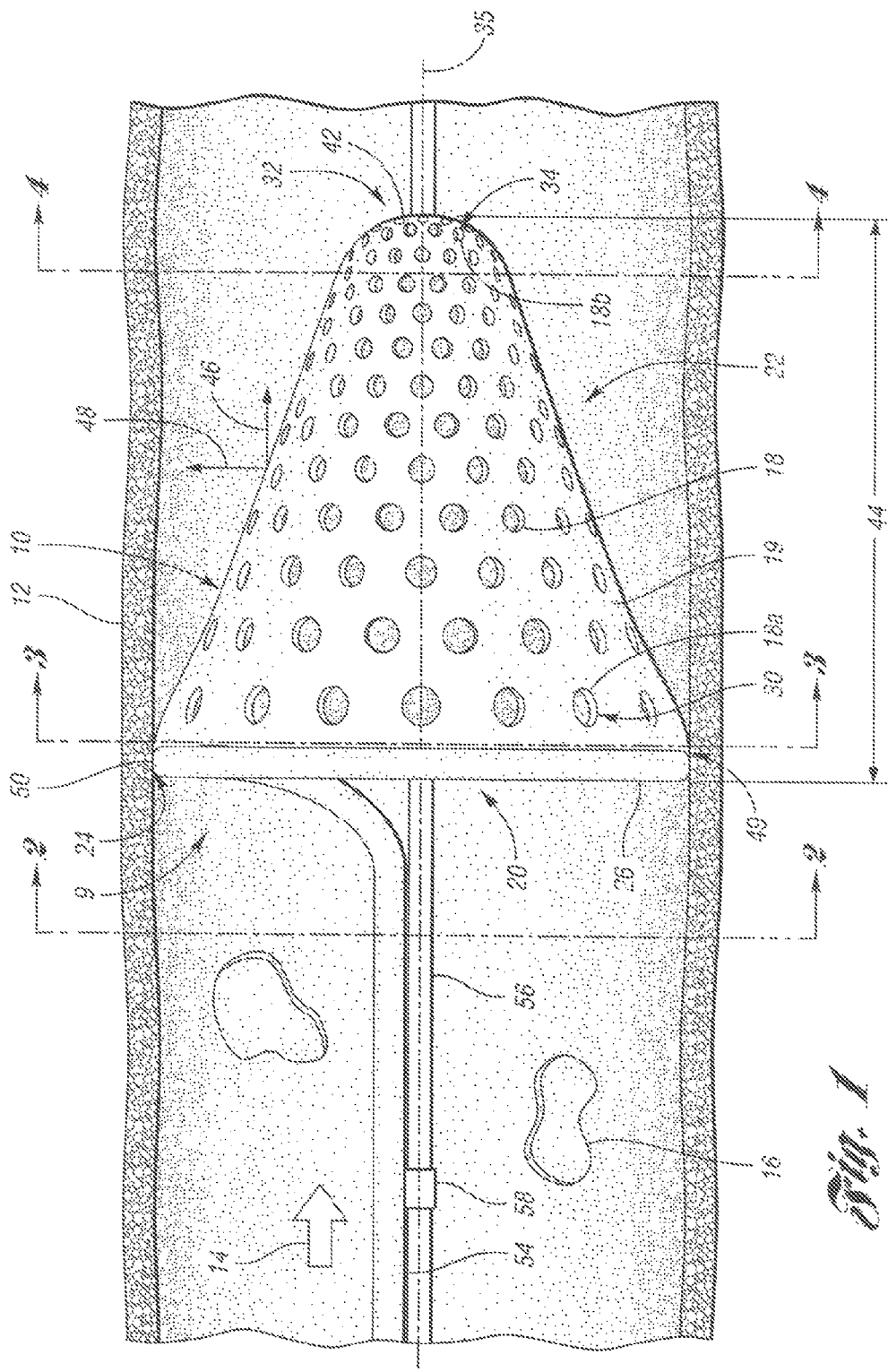

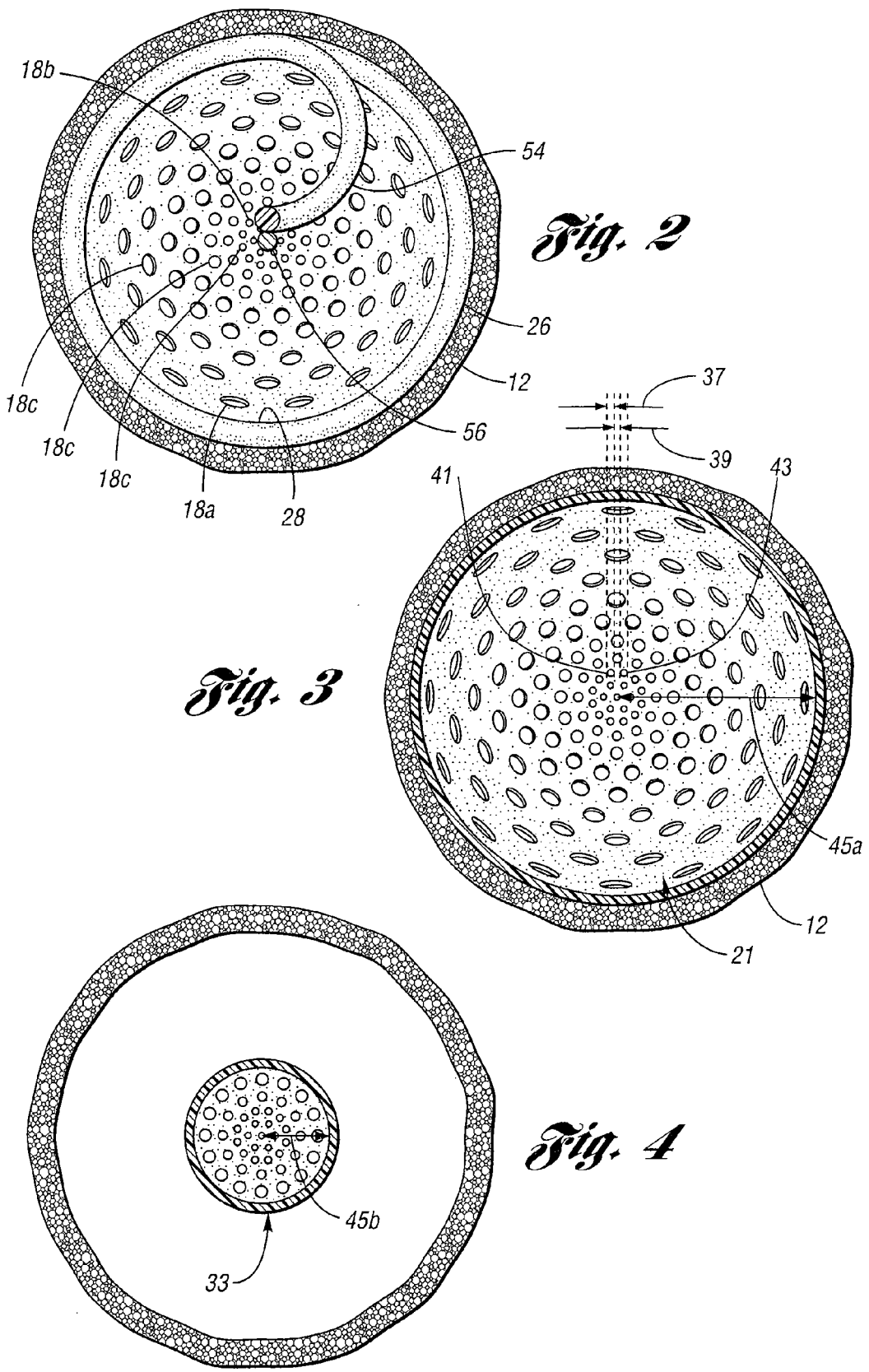

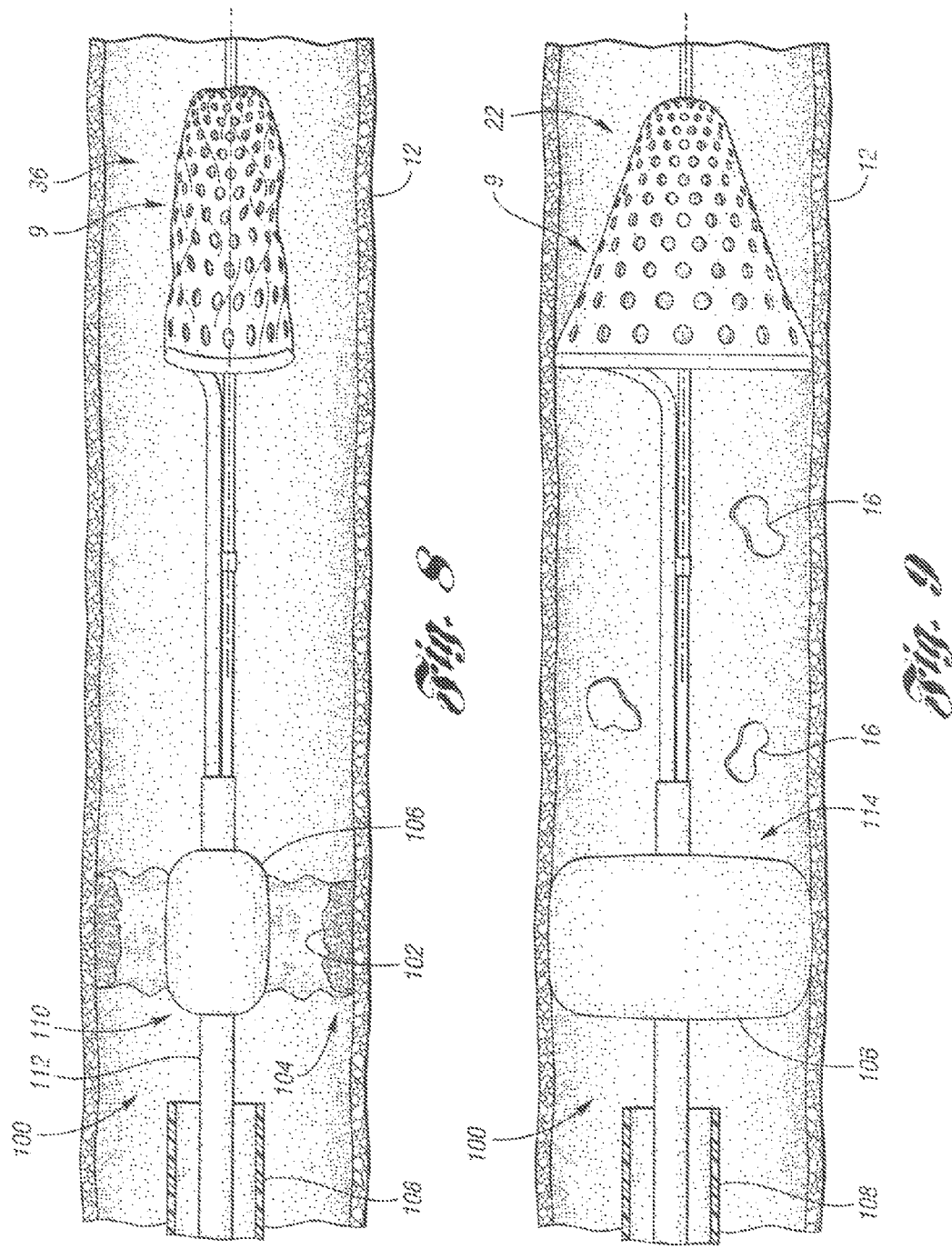

EMBOLIC PROTECTION DEVICE

CROSS-REFERENCE TO RELATED APPLICATION

This application claims benefit of U.S. Provisional Application No. 60/661,732, filed Mar. 15, 2005 entitled Embolic Protection Device.

BACKGROUND

1. Field of the Invention

The invention relates generally to medical devices. More specifically, the invention relates to intravascular embolic protection devices.

2. Related Technology

Embolic protection devices are percutaneously placed in a body vessel to prevent emboli from traveling and creating an undesirable embolism, e.g., pulmonary embolism. For example, vena cava filters are used for trapping emboli in the vena cava filter to prevent pulmonary embolism. Also, anti-platelet agents and anticoagulants may be used to breakdown blood clots. Moreover, snares and baskets (e.g., stone retrieval baskets) are used for retrieving urinary calculi. Additionally, occlusion coils are commonly used to occlude aneurysms and accumulate thrombi in a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall. During the stenosis procedure however, there is a risk of such blood clots and thrombi being undesirably released into the blood flow within the vasculature.

Therefore, embolic protection devices, such as occlusive devices and filters, have been developed to trap and to prevent the downstream travel of the blood clots and thrombi. The filters are typically advanced downstream of a site that is to be treated and then expanded into an opened state to increase the filter area. The blood clots and thrombi can be captured in the opened filter while blood is still able to flow therethrough.

However, filter devices may fail to completely open within the blood vessel, leaving gaps between the filter outer surface and the blood vessel inner surface. These gaps may permit the above-described blood clots and thrombi to flow past the filter, unoccluded. As a result, the unoccluded blood clots and thrombi may thereby compromise the blood flow at a location distal from the treatment site.

Thus, there is a need to improve the positioning the expanding of the filter device within the blood vessel to effectively capture the unoccluded blood clots and thrombi.

SUMMARY

In one aspect of the present invention, an embolic protection device for deployment in a body vessel is provided for filtering emboli in the body vessel. The device includes a filtering body having a lip and extending therefrom to a tail and a frame connected to the lip for supporting the filtering body. The filtering body includes first and second openings formed therethrough, the first opening having a first area for maintaining fluid flowpaths through the device, the second opening having a second area for filtering emboli in the body vessel. The first area is greater than the second area.

In another aspect of the invention, the first opening is one of a first plurality of openings located adjacent to the lip and the second opening is one of a second plurality of openings located adjacent to the tail. The filtering body further includes intermediate openings between the lip and the tail that are generally decreasing in size along a line extending from the lip to the tail. Additionally, the first, second, and intermediate openings are configured such that a fluid flowrate through the filtering body is substantially unhindered when openings adjacent to the tail become obstructed.

In yet another aspect, the frame includes a retrieval member extending from the frame to retrieve the embolic protection device from the body vessel. Furthermore, a tether is connected to an inner surface of the filtering body and is movable along an axis with respect to the connection means such as to create a collection area within the filtering body for collecting emboli. Additionally, a material promoting biofixation may be located around an outer surface of the filtering body to form a seal between the filtering body and the body vessel. More specifically, the material includes extracellular matrix that functions as a remodeling bioscaffold. Even more specifically, the material includes small intestinal submucosa.

In yet another aspect of the present invention, the embolic protection device is utilized in an assembly for removing emboli from a body vessel. The assembly further includes an emboli dislodging catheter for dislodging the emboli from an inner wall of the body vessel and causing the emboli to flow downstream, thereby becoming trapped within the filter body. The assembly also includes an outer catheter for delivering the emboli dislodging catheter into the blood vessel and a guide wire slidably coupled with the embolic protection device to guide the embolic protection device within the body vessel.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 1 is an environmental side view of an embolic protection device in an opened state within a blood vessel in accordance with one embodiment of the present invention;

FIG. 2 is a cross-sectional view of the embolic protection device in FIG. 1 taken along line 2-2;

FIG. 3 is a cross-sectional view taken along line 3-3 in FIG. 1, which is adjacent to the proximal end of the filter;

FIG. 4 is a cross-sectional view of the embolic protection device in FIG. 1 taken along line 4-4;

FIG. 8 is a side view of an embolic protection device utilized in an assembly for removing emboli from a blood vessel, in accordance with another embodiment of the present invention, before the emboli have been dislodged from the inner surface of the blood vessel; and FIG. 9 is a side view of the embolic protection device shown in FIG. 8 after the emboli have been dislodged from the inner surface of the blood vessel.

DETAILED DESCRIPTION

Figure 5:
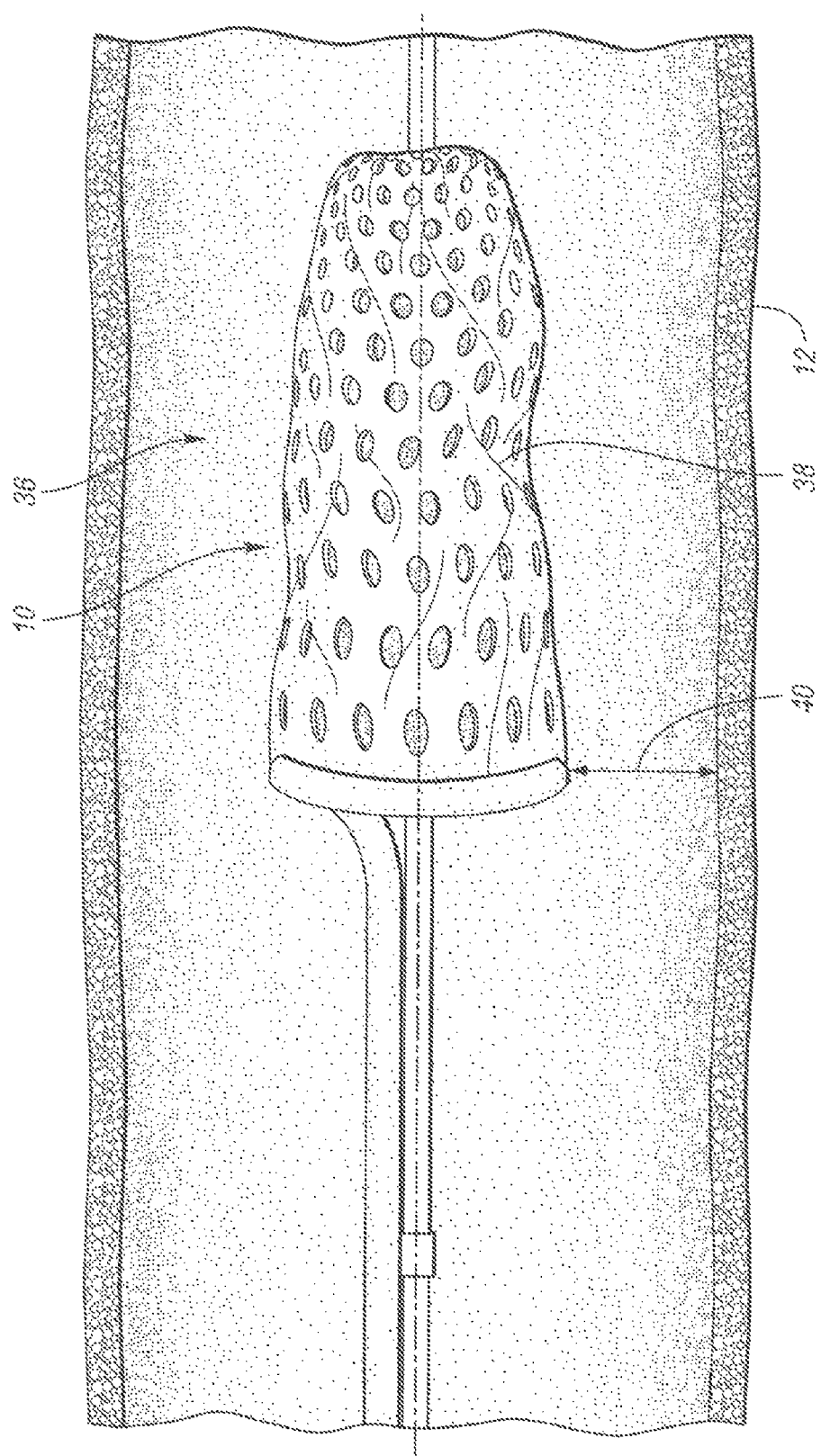
FIG. 5 is a side view of the embolic protection device in a closed state within a blood vessel in accordance with another embodiment of the present invention.

Embodiments of the present invention generally provide embolic protection devices, embolic protection apparatus, and methods for capturing emboli in a body vessel during angioplasty for treatment of a stenosis. One particular stenosis is a carotid artery stenosis. The embodiments solve the concerns of current stenosis treatments, such as the relatively high risks of surgery and the potential release of emboli into the vasculature during the stenosis procedure. Embodiments of the present invention provide a relatively low risk approach to capturing emboli released during a stenosis procedure, e.g., balloon angioplasty.

Referring now to the drawings, FIG. 1 shows an embolic protection device 9 to be positioned within a body vessel, such as a blood vessel 12 having a blood flow in a direction generally indicated by reference numeral 14. More specifically, the embolic device 9 includes a filtering body 10 positioned downstream of emboli 16, such as blood clots and plaque fragments, to trap and to prevent the downstream travel of the emboli 16, thereby reducing the likelihood of downstream blood vessels becoming blocked. As will be discussed in more detail below, the filtering body 10 includes openings 18 that permit blood to flow through and that prevent the emboli 16 from doing the same.

The filtering body 10 is composed of any suitable material 19, a woven mesh or net configuration, but any suitable material may be used. More specifically, the filter material 19 is preferably configured to avoid rupture and to be disposed within the blood vessel 12. Furthermore, the filter material 19 is preferably sufficiently flexible such that the filtering body 10 is able to conform to various shapes and configurations, as may be needed to engage the blood vessel 12.

The filtering body 10 preferably includes a proximally-located lip portion 20 that is substantially opened to an opened state 22 for receiving the emboli 16. More specifically, the lip portion 20 opens in the radial direction such as to form a substantially fluid-tight seal 24 with the blood vessel 12. The seal 24 substantially prevents emboli 16 from flowing around the filtering body 10 and causing the above-described conditions.

The lip portion 20 is held in the opened state 22 by a frame 26 that extends around the perimeter of the lip portion 20. The frame 26 shown in the Figures is a rigid wire formed into a generally circular loop 28 and having an adjustable diameter such as to conform to the inner surface of the blood vessel 12. Additionally, as shown in FIG. 5, the circular loop 28 is collapsible into a closed state 36 to be easily moved within the blood vessel 12 when desirable, such as during deployment into and during removal from the blood vessel 12. When in the closed state 36, the filter 10 has relatively small radial dimensions, and thus a gap 40 exists between the circular loop 28 and the blood vessel 12. Alternatively, other suitable designs may also be used.

In the area adjacent to the lip portion 20, the filtering body 10 includes proximal openings 18a, each defining a fluid flowpath for blood to flow there through. Additionally, each of the proximal openings 18a includes a cross-sectional area 30, configured to permit unoccluded blood to flow there through. The proximal openings 18a are preferably circular and are relatively spaced-apart from each other, but may have any suitable shape and configuration.

The filtering body 10 also includes a distally-located tail portion 32 that is closed-off in order to trap the emboli 16 that flow into lip portion 20 of the filtering body 10. However, similarly to the lip portion 20, the tail portion 32 includes distal openings 18b, each defining a fluid flowpath for blood to flow therethrough. Additionally, each of the distal openings 18b defines a cross-sectional area 34 large enough configured to permit unoccluded blood to flow there through.

The filtering body 10 preferably has a generally decreasing radius such that a first cross-sectional area 21 of the filtering body 10 (FIG. 3) taken along a plane adjacent to the lip portion 20 is substantially larger than a second cross-sectional area 33 of the filtering body 10 (FIG. 4) taken along a second plane adjacent to the tail portion 32. More specifically, the filtering body 10 is generally cone-shaped such as to have a generally constantly decreasing radius along a longitudinal axis 35.

The cross-sectional area 30 of each of the proximal openings 18a is substantially greater than the cross-sectional area 34 of the distal openings 18b in order to maximize the occluding capacity of the filtering body 10 and to promote full expansion of the filtering body 10 within the blood vessel 12, as is discussed in more detail below.

Regarding the tail portion 32, the distal openings 18b are relatively small such as to cause a flow resistance that is sufficient to open the filtering body 10. More specifically, the distal openings 18b are sized and positioned with respect to each other such that the filtering body 10 provides a flow resistance when the tail portion 32 is folded. As shown in FIG. 5, when the filtering body 10 is in a closed state 36, such as when being initially deployed into the blood vessel 12, the filtering body 10 may become folded along creases 38 such that some of the openings 18 become blocked. Therefore, the distal openings 18b are sized and positioned with respect to each other such as to provide a flow resistance unless substantially all of the distal openings 18b are unobstructed. For example, the distal openings 18b define a second diameter 37 and the filtering body 10 defines a spacer distance 39 between adjacent openings 41, 43 of the distal openings 18b; the spacer distance 39 is preferably equal to or greater than one half of the second diameter 37 such as to provide a resistance that is sufficient to open the filtering body 10. Even more preferably, the spacer distance 39 is equal to or greater than the second diameter 37. As another example, the distal openings 18b define a second area 47 and the filtering body 10 defines a spacer area 51 between adjacent openings 41, 43 of the distal openings 18b; the spacer area 51 is preferably equal to or greater than one half of the second area 47 such as to provide a resistance that is sufficient to open the filtering body 10. Even more preferably, the spacer area 51 is equal to or greater than the second area 47.

However, the distal openings 18b are preferably not so small as to restrict blood flow there through when the tail portion 32 is fully opened and unobstructed. As discussed above, restricted blood flow can cause various undesirable medical conditions. Therefore, the distal openings 18b are large enough such as to not reduce blood flow through the filtering body 10.

The distal openings 18b are preferably located along an end face 42 of the filtering body 10 that is substantially perpendicular to the direction 14 of the blood flow. This configuration also causes the filtering body 10 to fully open because the openings along the end face 42 have a maximum effective area when positioned to be perpendicular to the blood flow direction 14. Therefore, the natural properties of fluid flow will cause the cause the end face 42 to be perpendicular to the blood flow direction 14, thus opening the filtering body 10 to its full length 44 and maximizing its trapping volume.

Regarding the lip portion 20, the proximal openings 18a are relatively large to act as overflow passages for the distal openings 18b if they become obstructed. As emboli 16 flow into the filtering body 10 and engage the tail portion 32, the distal openings 18b may become obstructed, thereby limiting the fluid flow through the tail portion 32. To compensate for this reduced flow are, the proximal openings 18a have the relatively large cross-sections 30. Therefore, the large proximal openings 18a substantially prevent flow loss across the embolic protection device 9.

As shown in FIG. 2, intermediate openings 18c are located axially between the proximal and distal openings 18a, 18b such as to define flowpaths there through. The intermediate openings 18c are generally decreasing in size along the axial length 44 in the flow direction 14. Furthermore, the proximal openings 18a are generally more spaced-apart from each other than the distal openings 18b. Additionally, the intermediate openings 18c become generally less spaced-apart along the axial length 44 in the flow direction 14.

The proximal openings 18a may serve as continuously-used passages, such that blood continuously flows through the proximal openings 18a, whether the distal openings 18b are obstructed or unobstructed. However, due to the generally cone-shaped nature of the filtering body 10, the radially central portion of the filter receives the majority of the flow therethrough. More specifically, the natural fluid properties of the blood flow, such as friction between the blood flow and the blood vessel walls, cause the radially central portion of the blood vessel 12 to have a higher mass flow volume than the radially off-set portion of the blood vessel 12. Furthermore, the tapered shape of the filtering body 10 directs blood towards the tail portion 32 and thus towards the distal openings 34.

In addition to maximizing the trapping volume of and minimizing the flow losses through, the filtering body 10 also includes features that maximize the radial expansion of the embolic protection device 9. More specifically, to effectively form the seal 24 between the filtering body 10 and the blood vessel 12 and thus prevent emboli 16 from flowing past the filtering body 10, the embolic protection device 9 is configured such that blood flow causes the filtering body 10 to be radially opened until it engages the blood vessel 12 inner walls.

One such feature that radially opens the filtering body 10 is the generally cone-shaped design of the filtering body 10. More specifically, as shown in FIGS. 3 and 4, the filtering body 10 includes a radius 45a, 45b of generally diminishing size along the length 44 from the lip portion 20 to the tail portion 32. This shape causes blood flow along the direction 14 to create an axial force component 46 and a radial force component 48. More specifically, the axial force component 46 extends the filtering body 10 along its length 44, as discussed above. Furthermore, the radial force component 48 extends the filtering body 10 outwardly in the radial direction, towards the blood vessel 12 inner walls. Therefore, the cone-shaped nature of the filtering body 10 improves the seal 24 and increases the trapping volume of the device 9.

Figure 6:
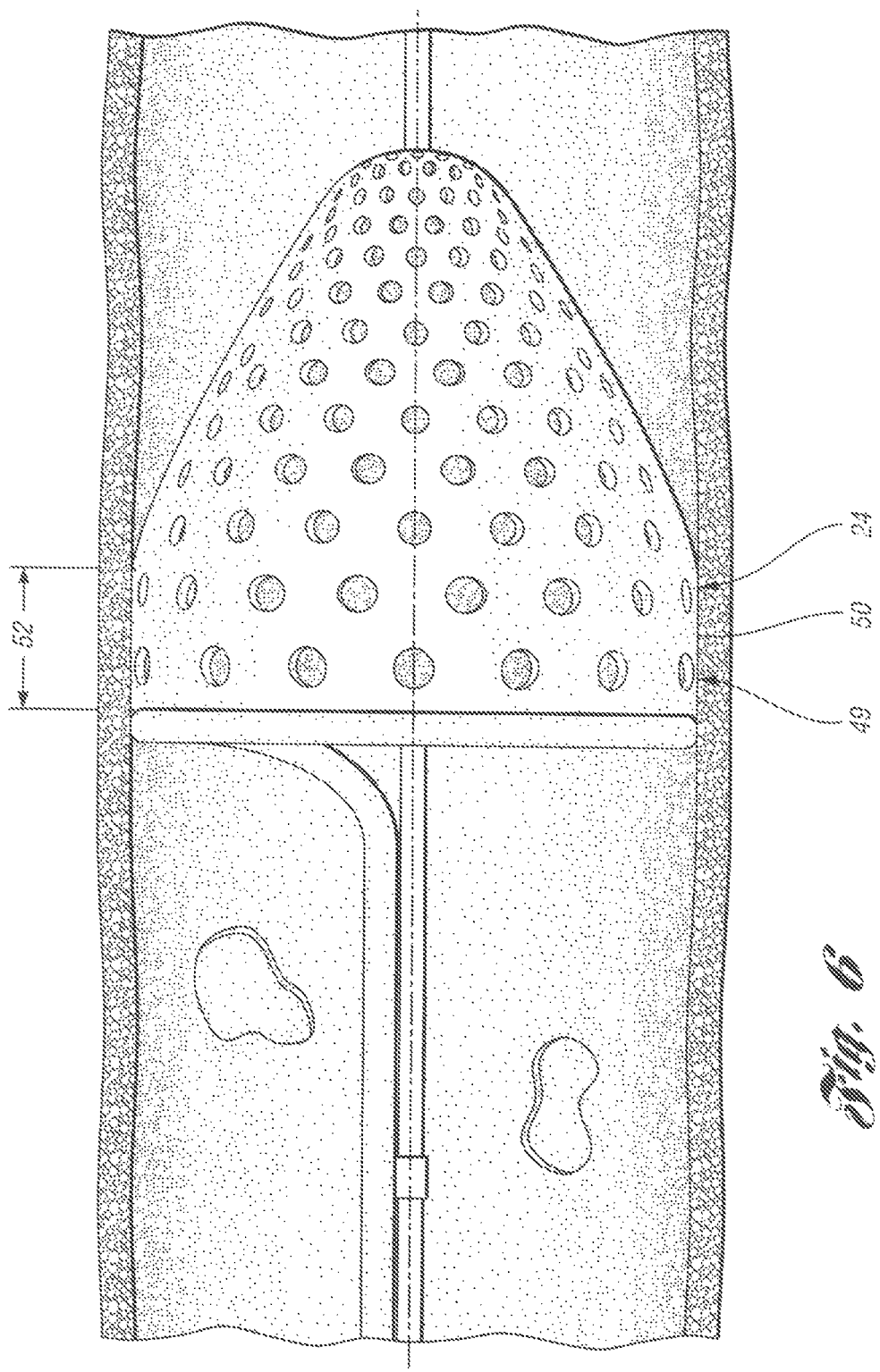
FIG. 6 is a side view of yet another embodiment of the embolic protection device.

Another such feature that radially opens the filtering body 10 is a material promoting biofixation between the filtering body 10 and the body vessel 12. More specifically, an outer surface 49 of the filter includes a connective tissue 50 that causes biofixation between the outer surface of the filtering body 10 and the inner surface of the blood vessel 12, thereby sealing the respective components 10, 12 together. The connective tissue 50 is located on the frame 26 and on a portion of the filtering body 10 immediately adjacent to the lip portion 20, as shown in FIG. 1. Additionally, as shown in FIG. 6, the connective tissue 50 may be located on the outer surface 50 along a length 52 of the filtering body 10 such as to increase the surface area of the seal 24.

Reconstituted or naturally-derived collagenous materials can be used as the connective tissue 50 in the present invention to induce tissue growth by the blood vessel. Such materials that are at least bioresorbable will provide advantage in the present invention, with materials that are bioremodelable and promote cellular invasion and ingrowth providing particular advantage. The connective tissue 50 preferably includes an extracellular matrix (ECM).

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Referring back to FIG. 1, the frame 26 is connected to, or unitarily formed with, a connecting wire 54 that is slidably coupled to a guidewire 56 to effectively deliver the filtering body 10 into the blood vessel 12. More specifically, as is known in the art, the guidewire 56 is metal wire that is generally rigid in the axial direction and that is generally flexible in the radial direction such that the guidewire 56 can be easily directed through a network of blood vessels. Furthermore, a connecting sleeve 58 includes an outer surface that is fixedly connected to the connecting wire 54 and an inner surface that is able to slidably receive the guidewire 56.

During delivery of the device 9 into the blood vessel 12, the guidewire 56 is first directed into the blood vessel 12 along the path of to a desired location, such as downstream of the site of a thrombus or a blood clot. Next, the device 9, being in the closed state 36, is slidably moved along the guidewire 56 via the connecting sleeve 58 until reaching the desired location. The device 9 is then expanded into the opened state 22 by any suitable means known in the art, such as by a catheter or other means.

Referring now to FIGS. 8 and 9, an assembly 100 for removing plaque and other stenotic lesions 102 from the blood vessel 12 is shown. The stenotic lesions 102 are fixed to the inner surface blood vessels 12, causing constricted areas 104 and thereby restricting bloodflow therethrough. The assembly 100 includes an emboli dislodging catheter, such as a balloon 106 that inflates to expand the flowpath of the blood vessel 12. More specifically, the balloon 106 expands to break-up the stenotic lesions 102 and cause fragments thereof to flow downstream as emboli 16.

During delivery of the balloon 106 into the blood vessel 12, an outer catheter 108 delivers the balloon 106 to the constricted area 104 in a deflated state 110, as is known in the art. The balloon 106 is then radially expanded by injecting a fluid, such as saline solution, into the balloon 106 via an inflating tube 112 fluidly connected thereto. The balloon 106 is then in an expanded state 114 to contact and break-up the stenotic lesions 102, thereby expanding the constricted area 104. The fragments of the stenotic lesions 102 then float downstream into the embolic protection device 9. Alternatively to the balloon, the emboli dislodging catheter may be any other suitable design for dislodging emboli, such as a scraping component or an expandable device.

The embolic protection device 9 is preferably expanded before the inflation balloon 106, so that the emboli 16 are prevented from bypassing the filter body 10. Additionally, the connecting wire 54 and the guidewire 56 in the Figures are received within the inflating tube 112, within a conduit that is fluidly-separated from the inflating chamber of the balloon, to control the delivery and the expansion of the embolic protection device 10.

Figure 7:
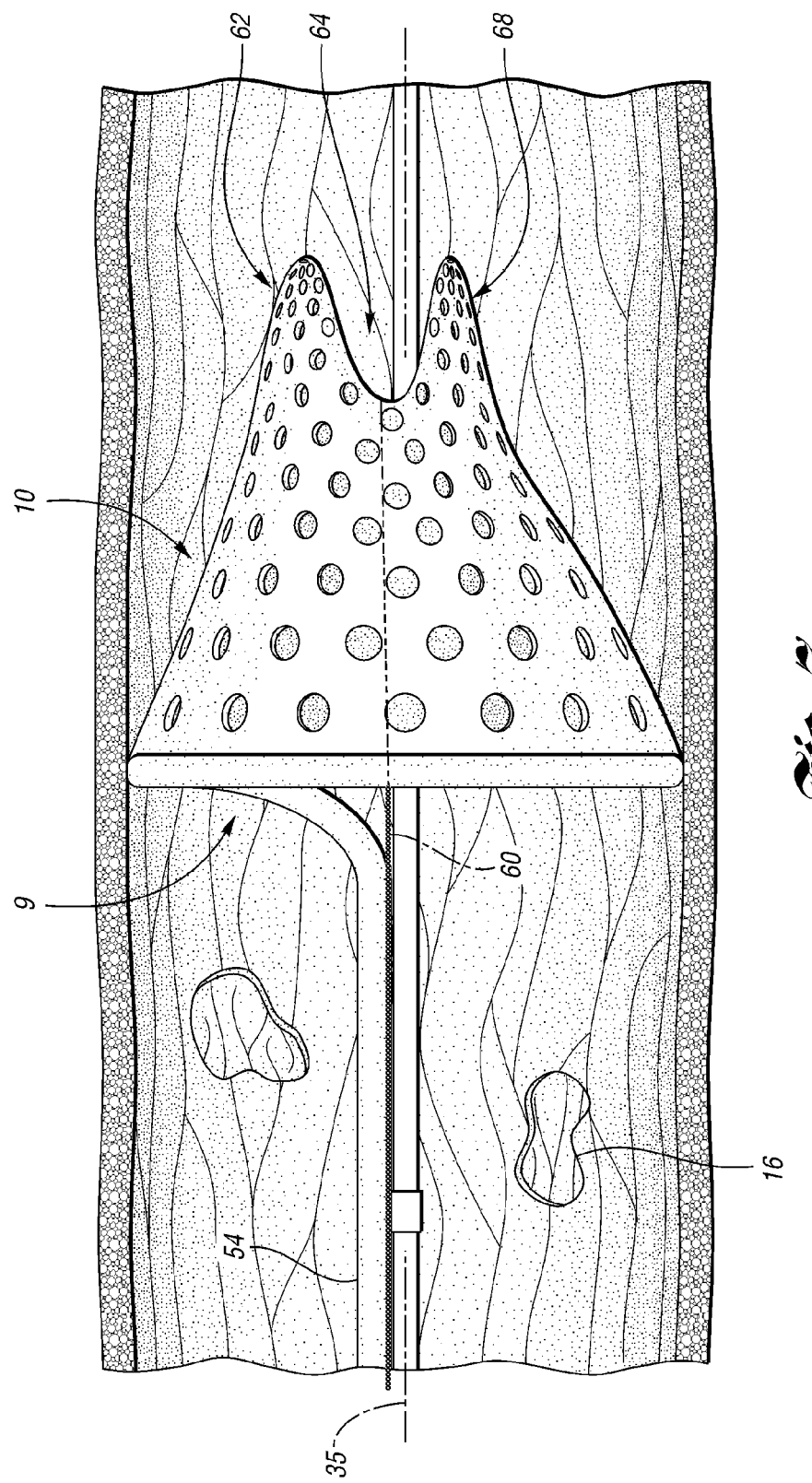
FIG. 7 is a side view of still another embodiment of the embolic protection device.

Referring now to FIG. 7, another alternative embodiment of the present invention is shown. The embolic protection device 9 in FIG. 7 includes a tether 60 that is connected to the inner surface of the filtering body 10 and that is slidable along the longitudinal axis 35 with respect to the connecting wire 54 to create a collection area 62 within the filtering body 10 for collecting emboli 16. More specifically, as the tether 60 is pulled against the direction 14 of the blood flow, the portion of the filtering body 10 that is connected to the tether 60 likewise moves against the blood flow. This movement creates an area, the collection area 62, within the filtering body 10 that is furthest downstream from the emboli 16, causing the emboli 16 collect within the collection area 62.

The tether 60 is preferably connected to a radially central portion 64 of the tail 32 such that the collection area 62 is radially off-set from the longitudinal axis 35. More specifically, the central portion of the tail 32 is pulled backwards such that the collection area 62 is a ring-shaped area surrounding the central portion 64. This configuration causes the emboli 16 to collect around the central portion 64 and leaves the central portion 64 substantially unobstructed. A plurality of tethers 60 may be used to create more collection areas.

It is therefore intended that the foregoing detailed description be regarded as illustrative rather than limiting, and that it be understood that it is the following claims, including all equivalents, that are intended to define the spirit and scope of this invention.

What is claimed is:

1. An embolic protection device for filtering emboli in a body vessel in which blood flows in a first direction along a blood flow path, the body vessel defining a central longitudinal axis, the device comprising:
a filtering body having a lip including a perimeter, the filtering body extending therefrom to a tail having an end face, the filtering body being configured to be folded into a closed state for delivery or retrieval and expanded into an open state for filtering emboli, the filtering body having a first plurality of openings formed therethrough and positioned generally spaced apart from each other and a second plurality of openings formed therethrough and positioned generally spaced apart from each other, the first plurality of openings being located adjacent to the lip, the second plurality of openings being located along the end face of the tail of the filtering body, the end face having a substantially perpendicular orientation that is substantially perpendicular to the first direction of the blood flow, the filtering body providing a flow resistance when the tail is folded, the substantially perpendicular orientation of the end face causing the filtering body to fully open into the open state when placed in the body vessel in the blood flow path, the first plurality of openings each having a first area for maintaining fluid flowpaths through the device and the second plurality of openings each having a second area for filtering emboli in the body vessel, wherein the first area is greater than the second area in both the closed state and the open state, and wherein the first plurality of openings is generally more spaced apart from each other than the second plurality of openings; and
a frame connected to the lip for supporting the filtering body, wherein the frame includes a wire formed into a loop that extends around the perimeter of the lip, wherein the frame perpendicularly opens in a radial direction along a plane perpendicular to the central longitudinal axis defining an opened state of the frame;
wherein the device further comprises a material promoting biofixation between the filtering body and the body vessel; and
wherein the material promoting biofixation includes extracellular matrix material that functions as a remodeling bioscaffold between an outer surface of the filtering body and an inner surface of the body vessel.

2. An embolic protection device as in claim 1, the filtering body further including a third plurality of intermediate openings located between the lip and the tail, the intermediate openings generally decreasing in size along a line extending from the lip to the tail.

3. An embolic protection device as in claim 2, wherein the first plurality of openings is configured such that a fluid flowrate through the filtering body is substantially unhindered when the second plurality of openings becomes obstructed.

4. An embolic protection device as in claim 1, wherein the second plurality of openings is radially closer than the first plurality of openings to the central longitudinal axis of the body vessel.

5. An embolic protection device as in claim 1, the filtering body having a generally tapered shape.

6. An embolic protection device as in claim 1, wherein the first area is at least two times larger than the second area.

7. An embolic protection device as in claim 1, the frame further including a retrieval member extending proximally therefrom to retrieve the embolic protection device from the body vessel.

8. An embolic protection device as in claim 1, further comprising a tether connected to the tail of the filtering body and being movable along the longitudinal axis to create a collection area within the filtering body for collecting emboli.

9. An embolic protection device as in claim 8, wherein the collection area is radially offset from the longitudinal axis.

10. An embolic protection device as in claim 1, wherein the material encircles the filtering body outer surface adjacent to the lip of the filter.

11. An embolic protection device as in claim 10, wherein the material is substantially located only along a portion of the filtering body adjacent to the lip of the filter.

12. An embolic protection device as in claim 1, wherein the extracellular matrix material includes small intestinal submucosa.

13. An embolic protection device as in claim 1, wherein each of the first and second plurality of openings is generally circular in shape.

14. An assembly for removing emboli from a body vessel in which blood flows in a first direction along a blood flow path, the body vessel defining a central longitudinal axis, the assembly comprising:
an emboli dislodging catheter configured for dislodging the emboli from an inner wall of the body vessel;
an outer catheter for delivering the emboli dislodging catheter into the body vessel;
an embolic protection device positioned distally of the emboli dislodging catheter for collecting the dislodged emboli in the body vessel, the embolic protection device including a filtering body having a lip including a perimeter, the filtering body extending therefrom to a tail having an end face, the filtering body being configured to be folded into a closed state for delivery or retrieval and expanded into an open state for filtering emboli, the filtering body having a first plurality of openings formed therethrough and positioned generally spaced apart from each other and a second plurality of openings formed therethrough and positioned generally spaced apart from each other, the first plurality of openings being located adjacent to the lip, the second plurality of openings being located along the end face of the tail of the filtering body, the end face having a substantially perpendicular orientation that is substantially perpendicular to the first direction of the blood flow, the filtering body providing a flow resistance when the tail is folded, the substantially perpendicular orientation of the end face causing the filtering body to fully open into the open state when placed in the body vessel in the blood flow path, the first plurality of openings each having a first area for maintaining fluid flowpaths through the device and the second plurality of openings each having a second area for filtering emboli in the body vessel, wherein the first area is greater than the second area in both the closed state and the open state, and wherein the first plurality of openings is generally more spaced apart from each other than the second plurality of openings; and
a frame connected to the lip for supporting the filtering body, wherein the frame includes a wire formed into a loop that extends around the perimeter of the lip, wherein the frame perpendicularly opens in a radial direction along a plane perpendicular to the central longitudinal axis defining an opened state of the frame;

wherein the device further comprises a material promoting biofixation between the filtering body and the body vessel; and wherein the material promoting biofixation includes extracellular matrix material that functions as a remodeling bioscaffold between an outer surface of the filtering body and an inner surface of the body vessel; and a guide wire slidably coupled with the embolic protection device to guide the embolic protection device within the body vessel.

15. An assembly as in claim 14, further comprising a connecting wire unitarily formed with the frame, the connecting wire being slidably coupled to the guidewire for effective delivery of the embolic protection device into the blood vessel.

\* \* \* \* \*